United States Patent [19]

Genshaw et al.

[11] Patent Number: 5,106,753
[45] Date of Patent: Apr. 21, 1992

[54] METHOD FOR DETERMINING MANGANESE LEVEL IN BLOOD USING A PORPHYRIN COMPOSITION

[75] Inventors: Marvin A. Genshaw, Elkhart; Michael J. Pugia, Granger, both of Ind.

[73] Assignee: Miles Inc., Elkhart, Ind.

[21] Appl. No.: 468,665

[22] Filed: Jan. 23, 1990

Related U.S. Application Data

[63] Continuation-in-part of Ser. No. 301,488, Jan. 26, 1989, abandoned.

[51] Int. Cl.$^5$ ............................................. G01N 33/70
[52] U.S. Cl. ........................................ 436/74; 424/617; 514/22; 514/183; 514/184
[58] Field of Search ............... 436/74, 84, 164, 175, 436/177, 178, 183, 904, 73, 85, 98, 92, 530, 531, 528; 424/617; 514/22, 183, 184

[56] References Cited

PUBLICATIONS

Masaaki Tabata; "Kinetic Method for the Determination of Nanogram Amounts of Lead (II) Using its Catalytic Effect on the Reaction of Manganese (II) with 5, 10, 15, 20-tetrakis (4-sulphanotophenyl)porphine"; Analyst, Feb. 1987 vol. 112 pp. 141-144.

Gelb, M. H.; Toscano, W. A.; Shgar, S. G.; "Chemical mechanisms for cytochrome P-450 oxidation: Spectral an catalytic properties of a manganese-substituted protein"; Proc. Natl. Acad. Sci. USA, vol. 79, pp. 5758-5762, Oct. 1982

Hagime Ishii; Hidemasa Koh; Katcuhiko Satoff; "Spectrophotometric determination of Manganese Utilizing Metal Ion Substitution in the Cadmium-$\alpha,\beta,\gamma,\delta$-Tetrakis(4-Carboxyphenyl)Porphine Complex", Analytica Chimica Acta, 136(1982) 347-352.

Primary Examiner—David L. Lacey
Assistant Examiner—Thomas E. Daley
Attorney, Agent, or Firm—Roger N. Coe

[57] ABSTRACT

The present invention is directed to a simple and inexpensive liquid or dry reagent assay system for detecting nanomolar amounts of manganese in body fluids in microgram per liter concentrations. More specifically, the manganese assay of this invention is directed to the optical detection of a chromogenic reaction, such as the oxidation of a redox indicator, catalyzed by a manganese porphyrin complex.

1 Claim, 6 Drawing Sheets

METHOD FOR DETERMINING MANGANESE LEVEL IN BLOOD USING A PORPHYRIN COMPOSITION

RELATED APPLICATION

This is a continuation-in-part of Ser. No. 301,488, filed Jan. 26, 1989, now abandoned.

BACKGROUND OF THE INVENTION

1. Field of the Invention

The present invention is directed to a simple and inexpensive liquid or dry reagent assay system for detecting manganese in body fluids in microgram per liter concentrations. More specifically, the manganese assay of this invention is directed to the optical detection of a chromogenic reaction, such as the oxidation of a redox indicator, catalyzed by a manganese porphyrin complex. Sufficient oxygen, in a concentration near the saturation value or in the form of free access to air, must be present.

2. Discussion of the Prior Art

Manganese is known to be a cofactor in certain biochemical enzymatic systems, such as the glycosyl transferases (enzymes which are necessary for polysaccharide and glycoprotein synthesis). Manganese is also involved in cholesterol biosynthesis and therefore manganese deficiency can cause decreased serum cholesterol.

Although iron, zinc, and copper are considered essential because clinical evidence of deficiency exists, manganese is generally accepted as essential for humans on the basis of its proven role in manganese-dependent enzymes rather than on direct evidence of human deficiency. Manganese supplementation is sometimes necessary to alleviate blood clotting defects and hypocholesterolemia in manganese-deficient experimental lab animals. It has been postulated that manganese-dependent glycosyl transferase activity may be needed for synthesis of normal prothrombin, a glycoprotein.

Manganese metal enzymes incorporate manganese in the +2 or +3 valence state and include pyruvate carboxylase and superoxide dismutase. Known manganeseactivated enzymes include hydrolases, kinases, decarboxylases, and transferases.

Manganese is absorbed in the small intestine, but absorbance can be hindered by calcium, phosphorus, ferric citrate, and soy protein. Manganese deficiency can also be caused by dietary deficiency or by metal ion competitors, such as copper, iron and magnesium.

However, manganese homeostasis appears to be regulated through adjustments in body excretion rather than by intestinal absorption. The liver can typically adjust the amount of manganese in the body by altering the amount of biliary excretion. Average manganese dietary intakes generally vary from about 2.5-8.3 mg/d (milligrams per day). The estimated adequate and safe intake of manganese is about 2.5-5.0 mg/d for adults.

Chronic manganese poisoning has occurred in miners, foundry workers, welders, and workers manufacturing drugs, pottery, ceramics, glass, varnish, and food additives. The symptoms are schizophreniclike psychiatric effects and neurological disorders clinically similar to Parkinson's disease. The similarity between symptoms of manganese poisoning and Parkinson's disease has led to the discovery of a link between manganese and catecholamine metabolism. Decreases in striatal dopamine are seen in both syndromes, and administration of L-dopa (adopamine precursor) is effective in alleviating several of the common symptoms of Mn poisoning. Treatment of human manganese intoxications may also include various therapies for respiratory symptoms and the administration of metal chelators such as EDTA to reduce physiological burden.

Serum manganese levels typically increase following industrial exposure, acute hepatitis, and myocardial infarction. Suggestions have been made that manganese levels may relate to bone defects and a number of other physiological problems. As a result, determining manganese levels in body fluid provides valuable medical information and certainly will provide valuable medical information in the future when more is known of the medical significance of this ion.

Determining Manganese

The most common analytical techniques for determining manganese in biological specimens are neutron activation analysis (NAA), emission spectroscopy (ES), and atomic absorption spectrophotometry (AAS). A less common method is described in "Determination of Trace Metals in Marine Biological Reference Materials by Inductively Coupled Plasma Mass Spectrometry," *Anal. Chem.* 60, pp. 687–691 (1988), in which inductively coupled plasma mass spectrometry (ICP-MS) is discussed as a method for metal determination. Yet another method is described in "Simultaneous Multielemental Analysis of Some Environmental and Biological Samples by Inductively Coupled Plasma Atomic Emission Spectrometry," *Anal. Chem.* 60, pp. 1033–1042 (1988), relating to a Parr bomb technique for sample preparation followed by simultaneous inductively coupled plasma atomic emission spectroscopy [ICP-AES]. For the clinical laboratory, however, the AAS technique is most common for the determination of manganese. Indeed, in "An Analysis for Blood Manganese Used to Assess Environmental Exposure," by Hams and Fabri, *Clinical Chemistry*, 34, No. 6, pp. 1121–1123, (1988) the recommended method for determining manganese concentration in blood is by AAS.

Analysis using any of the above methods requires expensive instrumentation which must be operated by a trained technician. The complex and sophisticated instruments can be susceptible to failure and typically require periodic calibration and service. Costs associated with measuring manganese on a commercial scale with conventional technology can be very high and include the initial cost of the instrument, the cost of a trained technician to operate the instrument, and the service costs in maintaining the instrument.

Although wet chemistry methods are also available, such as a modified Fernandez method described in Henry, et al., *Clinical Chemistry*, Chapter 19, pp. 708–712, these wet chemistry methods are typically time-consuming, laborious, multistep methods which are very susceptible to ion interference, and are typically very inconvenient because special care must be taken to avoid ion contamination, i.e., all water must be redistilled in an all glass distillation apparatus and similar-type inconvenient laboratory preparation.

A relatively simple assay system for determining manganese has been found which uses a particular indicator, 1-(2-pyridylzao)-2-Napthol(PAN), [the solvent extraction of metal chelates, Jiri Stary, Pergamon Press, New York, 1964, pages 129,130] which will bind to manganese (II) in a 3:1 complex, thereby providing a color change. This "PAN" method however is not sensitive to low concentrations of manganese.

Manganese Complexing

Many metal ions, including manganese, react with electron pair donors to form coordination compounds or complex ions. The donor species (ligand) must have at least one pair of unshared electrons available for bond formation. Water, ammonia, and halide ions are common ligands. Although exceptions exist, a specific cation ordinarily forms coordination bonds to a maximum of two, four, or six, its coordination number being a statement of this maximum. The species formed as a result of coordination can be electrically positive, neutral, or negative.

Manganese can form a complex with porphyrins (a class of compounds related to the iron-free decomposition product of hematin), such as in [5,10,15,20-tetrakis(2,6-dimethyl-3-sulfonatophenyl)porphinato]-manganese (III). This particular manganese porphyrin complex has been shown to cause catalase-like conversion of hydrogen peroxide to water and oxygen between a pH of 7.6 to 12.1. See generally, Balasubramanian, et al., "Catalase Modeling. 2. Dynamics of Reaction of a Water Soluble and Non $\sim$-Oxo Dimer Forming Manganese(III) Porphyrin with Hydrogen Peroxide," *J. Am. Chem. Soc.* 109, pp.7865–7873 (1987). However, the Balasubramanian article is directed to the kinetics of the Mn-porphyrin catalase-type reaction and is not directed to a method for assaying manganese. The Balasubramanian method uses a stop flow device necessary for short lived colored products and is a method which is not usable for a Mn assay. It should also be noted that very high concentrations of manganese porphyrin were used ($10^{-6}$ to $10^{-5}$M) Any color formed is transient and very unstable. This is because 2,2'-azinobis(3ethylbenzthiazoline sulfonic acid) (ABTS) is very unstable at alkaline pH. For a pH of 8 or greater the blue color produced by ABTS fades rapidly.

Osteoporosis

The manganese assay of this invention is useful in diagnosing and treating osteoporosis and other bone disorders. A short discussion of osteoporosis is therefore provided below.

Osteoporosis is a physiological condition characterized by a reduction of bone mass. The disorder is believed to cause some 1.3 million fractures per year in individuals over age 45 at a cost of at least $7–10 billion. Postmenopausal women are among those most affected by this disorder. The National Institute on Aging estimates that this condition afflicts about half of women over age 45 and 90 percent of those over age 75.

Presently, there are no widely recognized blood or urine tests to diagnose osteoporosis, although laboratory tests do exist which diagnose primary osteoporosis o identify risk factors associated with it. Hypogonadism, a risk factor for primary osteoporosis in both men and women, can be identified by some lab tests which assess gondal function, including measurements of luteinizing hormone, follicle-stimulating hormone, and estradiol levels in women and free testosterone levels in men.

Currently, osteoporosis is diagnosed primarily by radiologic methods, including quantitative computed tomography and single or dual photon absorptiometry. However, these methods have limited usefulness, because they reveal bone loss only after it has occurred.

Other chemistries which can also be measured in patients with osteoporotic symptoms include serum calcium, inorganic phosphate, and alkaline phosphatase levels. Since calcium levels are typically normal in primary osteoporosis, abnormalities may indicate other disease processes which are causing osteoporotic symptoms. Serum alkaline phosphatase levels correlate to some extent with the activity of osteoblasts—the cells involved in bone production —because osteoblasts contain alkaline phosphatase. However, the test is not helpful in diagnosing osteoporosis, because alkaline phosphatase levels are normal in osteoporosis patients, unless they have had recent fractures.

Osteocalcin levels can be measured and fluctuate somewhat with bone activity, since levels are increased in children and adolescents. However, these levels also tend to be normal in patients with osteoporosis.

Protein electrophoresis can be conducted to determine if the osteoporotic symptoms are due to multiple myeloma, which may be causing symptoms similar to osteoporosis. Serum and urine protein electrophoresis will uncover about 99 percent of multiple myeloma cases.

Although many risk factors, including female gender, slender build, early menopause, and Caucasian race, are associated with osteoporosis, its exact etimology is unknown. Bone mass is believed to peak at about age 30, when calcium begins to be lost from bones faster than it is replaced, causing bones to become less dense.

A key problem slowing the development of laboratory tests to diagnose primary osteoporosis is that the bone in affected individuals is histologically abnormal—to show this a bone biopsy is needed.

Manganese And Bone Metabolism

In a published article, "Role of Manganese in Bone Metabolism", by Strause and Saltman, reprinted from ACS Symposium Series No. 354, "Nutritional Bioavailability of Manganese", 1987, the authors suggest that low manganese concentration in blood serum may relate to osteoporosis and perhaps other bone conditions. The article indicates that serum manganese levels of normal women are about $0.04 \pm 0.03$ mg/L (milligrams per liter) and the levels for osteoporotic women are about $0.02 \pm 0.004$ mg/L.

However, normal manganese levels in serum are commonly believed to be in the range of about 0.0017–0.0005 mg/L (rather than the $0.04 \pm 0.03$ mg/L suggested by the Strause article), and the commonly accepted values for normal serum manganese concentration substantially overlap with the manganese levels reported by Straus for osteoporotic women (0.01 mg/L). Therefore, although the Strause article suggests a correlation between manganese serum concentration and osteoporosis, a closer look at the article shows no correlation of clinical significance. A 0.01 mg/L serum manganese concentration provides little, if any, assistance in determining whether a person with this manganese level does or does not have osteoporosis.

OBJECTS OF THE INVENTION

It is an object of the present invention to provide a dry or liquid manganese assay which is sensitive to microgram per liter concentrations of manganese.

A further object of the present invention is to provide a manganese assay which is easy to use, reliable, and inexpensive to manufacture on a large scale.

A further object of the present invention is to provide a sensitive manganese assay which can accurately determine manganese levels in body fluids and which aids in the diagnosis and treatment of osteoporosis.

A yet further object of the present invention is to provide an assay for the determination of manganese in the environment.

Other objects and features of the present invention will become apparent to those of ordinary skill in the art upon reading the following specification.

BRIEF DESCRIPTION OF THE DRAWINGS

Other and further objects, advantages and features of the invention will be apparent to those skilled in the art from the following detailed description thereof, taken in conjunction with the accompanying drawings in which.

DETAILED DESCRIPTION OF THE PREFERRED EMBODIMENTS

Figure 1:
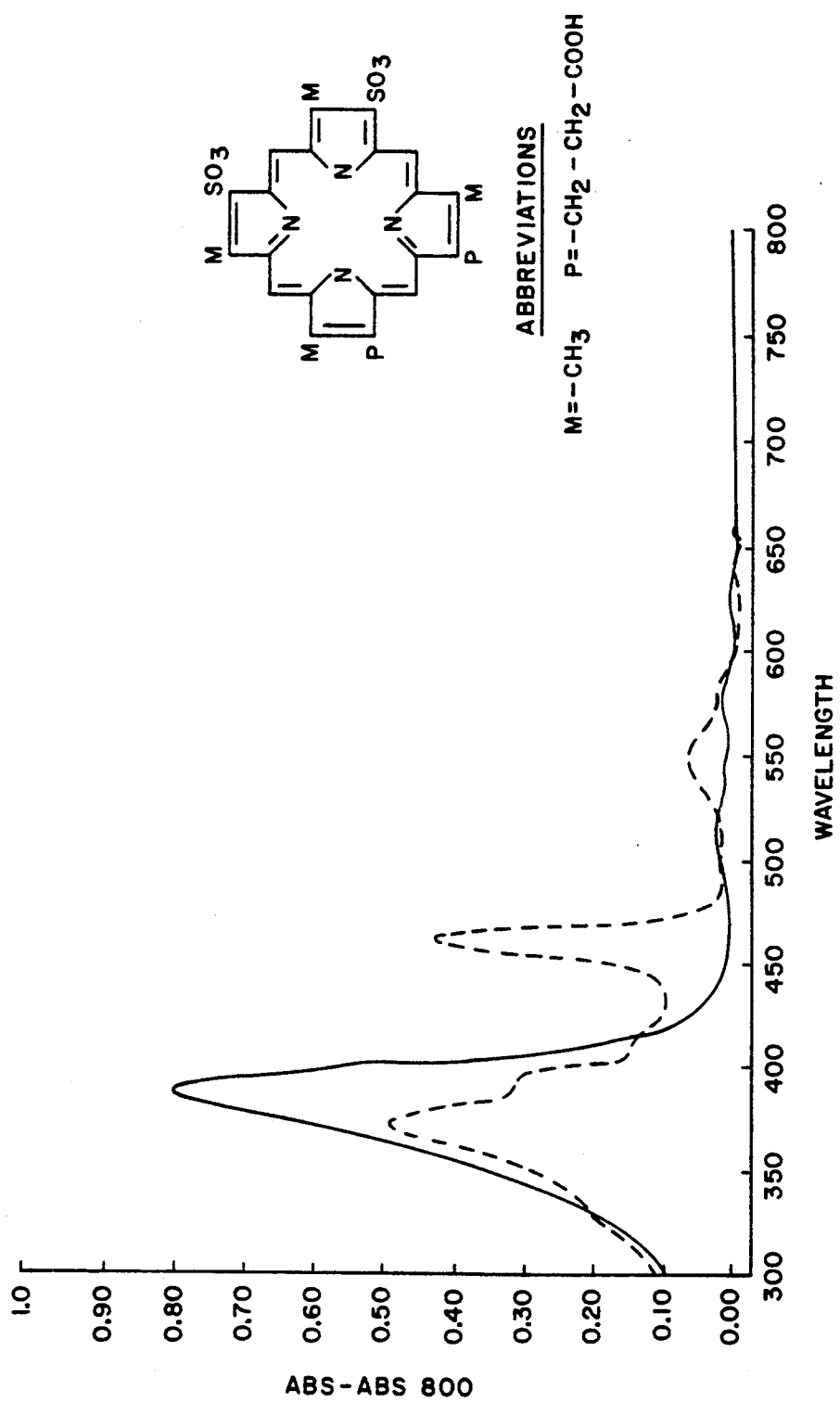
FIGS. 1 to 5 show absorbance spectra in accordance with Example IV.
Figure 2:
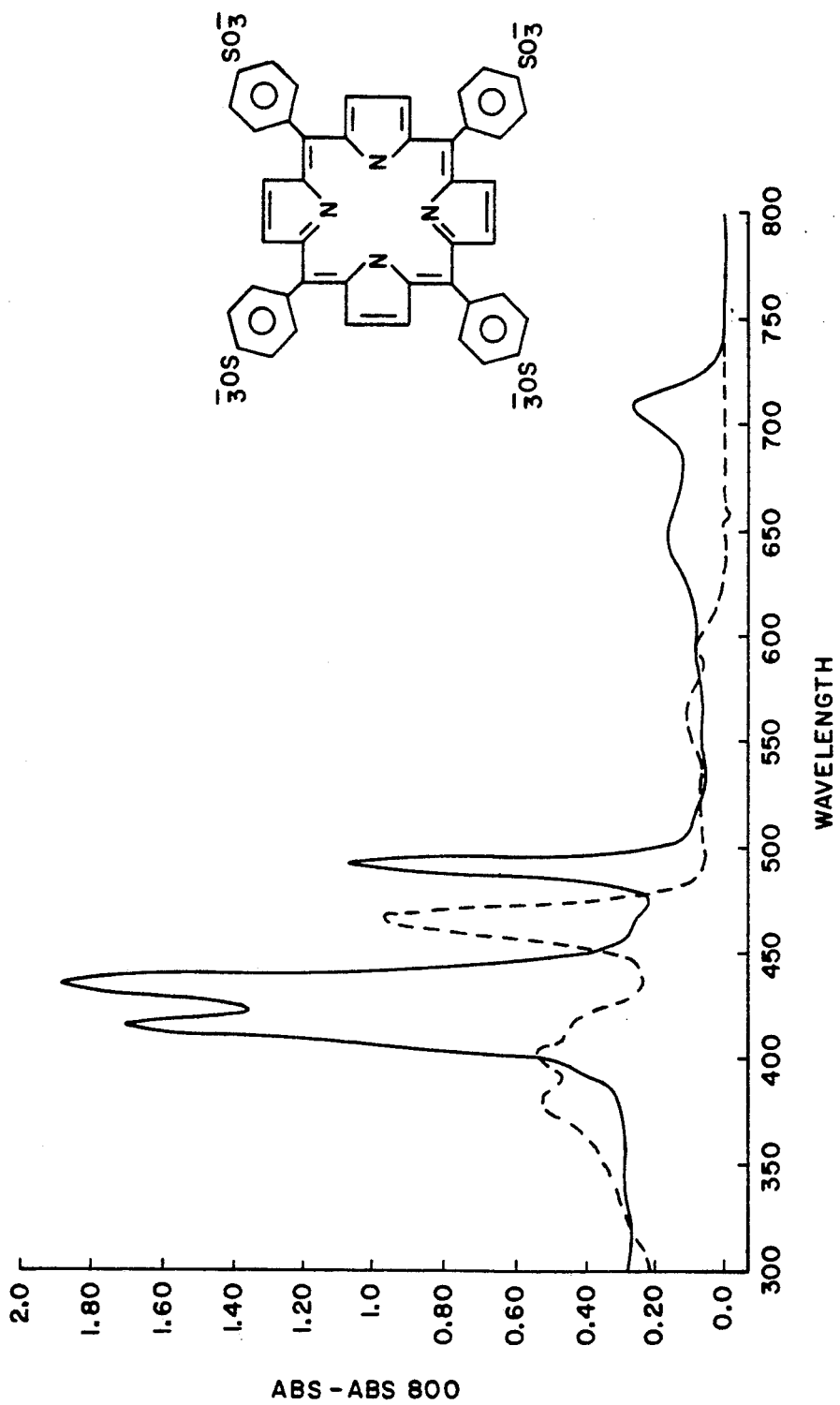
Figure 3:
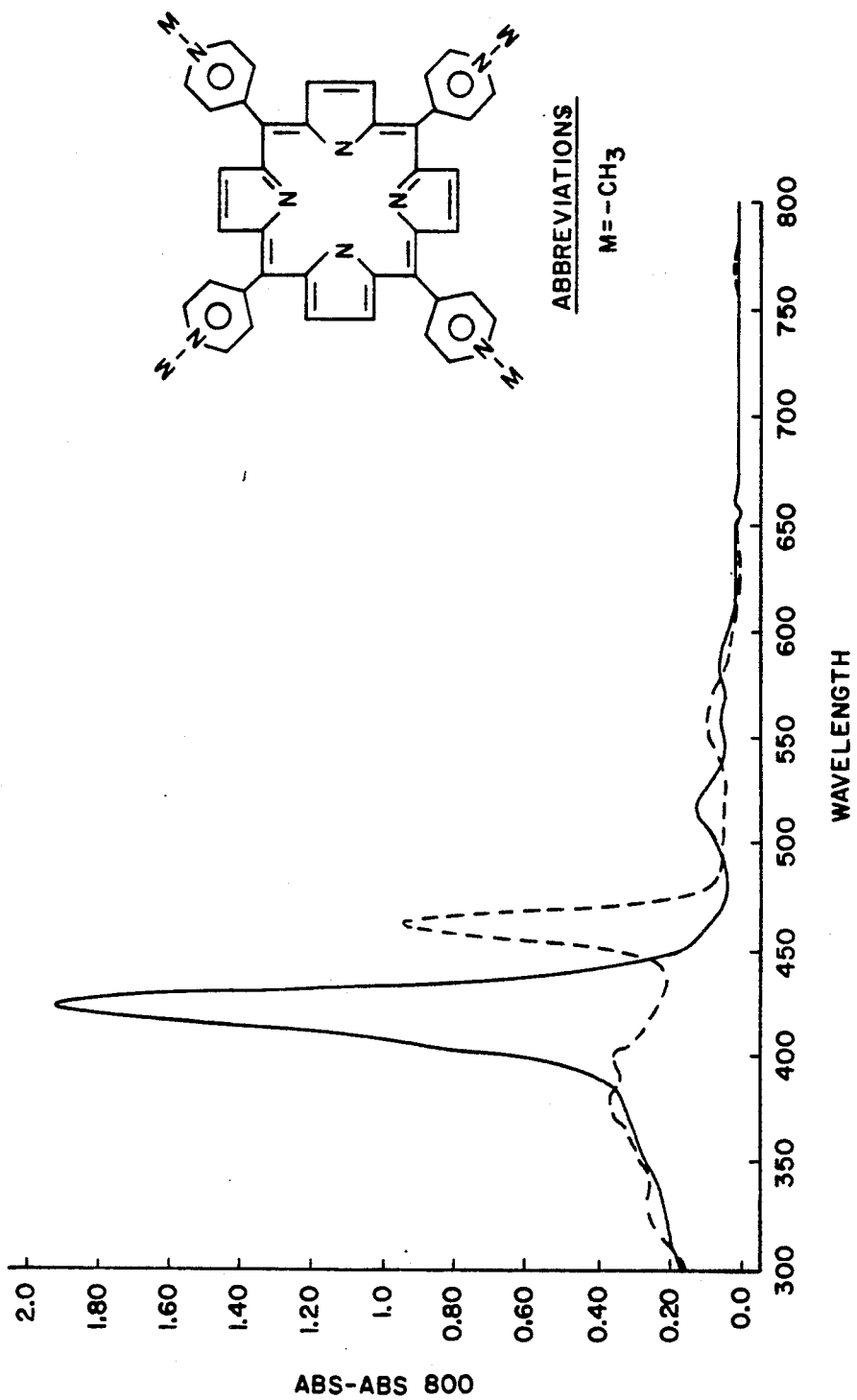
Figure 4:
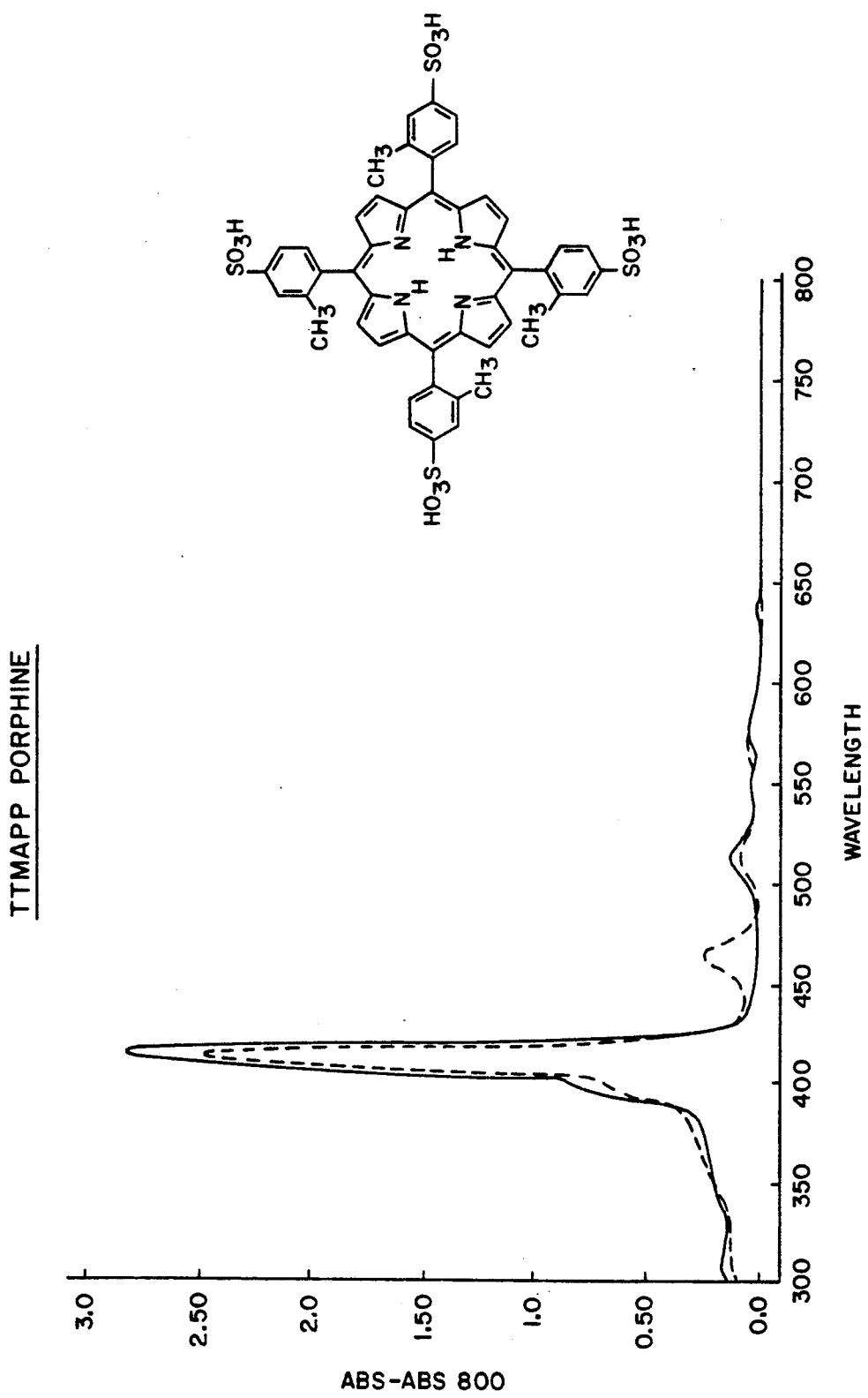
Figure 5:
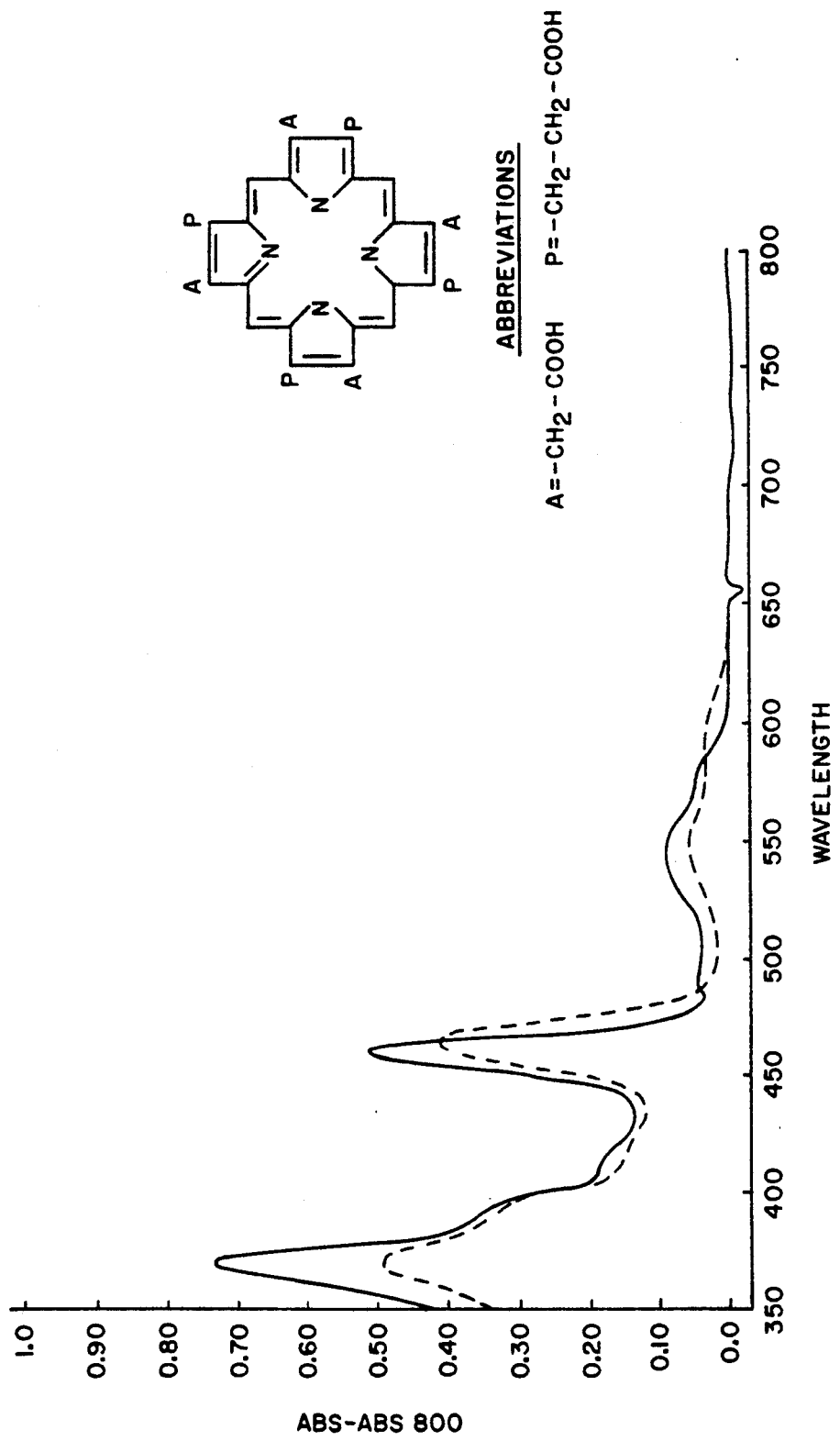

The present invention is directed to a diagnostic test using a Mn(III) porphyrin complex [5 nM (nanomolar) to 0.1 mM (millimolar)] to catalyze the oxidation of a redox or similar type indicator (1 to 100 mM). Unlike many conventional assay systems, hemoglobin will not significantly interfere with the reagent system of the present invention. In the present invention, no peroxide or hydroperoxide is created by the assay's reagent system. Oxygen is used as the oxidant in the system. The oxygen concentration must be sufficient for the reaction since otherwise the reaction is limited by the oxygen rather than the manganese porphyrin. The oxygen concentration should be near the saturation value or the reagent should have access to air (as in a strip format). This means the range is from 0.25 (air) to 1.25 (pure oxygen) millimolar. Accelerators (e.g., quinolines, pyridines, etc.), buffers and inhibitors (e.g., azides, cyanides, etc.) may be present in the system.

In the presence of manganese, the reagent system of the invention creates a colorimetric response. The manganese will complex with the porphyrin and catalyze the oxidation of the redox indicator. Manganese porphyrin complexes which occur naturally in body fluids will be detected equally as well and do not require complexation by a synthetic porphyrin. Since the manganese acts as a catalyst, very small amounts, micrograms per liter concentrations, will cause a colorimetric response, and as a result, the assay system is extremely sensitive. Furthermore, the reagent system of the present invention is a simple, single step reagent system which is not only accurate but does not require expensive instrumentation or a trained technician.

The analyte of interest, manganese, will complex with porphyrins as follows:

Mn + porphyrin ⇌ Mn.porphyrin

The manganese catalyzed reaction is illustrated as follows:

Mn.porphyrin + $O_2$ ⇌ Mn.porphyrin.$O_2$ $2H^+$ + Mn.porphyrin.$O_2$ ⟶ (porphyrin$^+$)Mn=O + $H_2O$ -continued (porphyrin$^+$)Mn=O + Indicator $\xrightarrow{\text{Redox} \atop \text{Fast}}$ (porphyrin)Mn=O + Oxidized Indicator (porphyrin)Mn=O + Indicator + $2H^+$ $\xrightarrow{\text{Redox} \atop \text{Fast}}$ (porphyrin)Mn + Oxidized Indicator + $H_2O$ The range of the assay has been demonstrated from 1.0–50,000 μg/L. Expected values for manganese in various samples are:

| | Ref Values |
|---|---|
| Water | 50.0 μg/L (allowable level) |
| Blood | 8.0–18.7 μg/L |
| Urine | 0.1–20.0 μg/L |
| Serum | 0.54–1.76 μg/L |

The porphyrins which can be used in this invention are as follows:

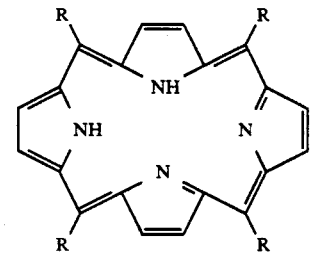

Where R is

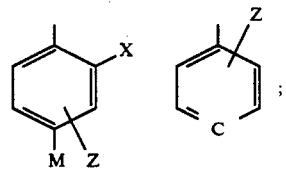

X = $CH_2$, $CH_2CH_3$, or $CH_2CH_2CH_3$, or;
M = $CO_2H$, $PO_3H_2$, or $SO_3H$;
Z = H, $CH_3$, $CH_2CH_3$, $CH_2CH_2CH_3$, $OCH_3$, $NO_2$, $CO_2H$, $NH_2$, Cl, Br, or F;

or

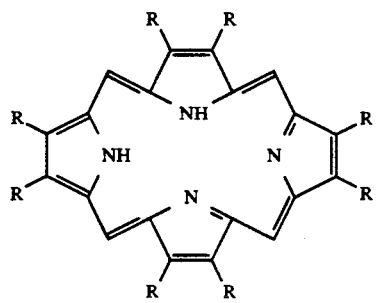

Where each R is independently selected from $CH_3$, $CH_2CH_3$, $CH_2CH_2CH_3$, $CH_2CH_2CO_2H$, $CH_2CO_2H$, $CH_2CH_2PO_3H_2$, $CH_2CH_2SO_3H$, $CH_2CH_2OH$, $CH_2CH_2NH_2CH_2CH=CH_2$, CHOHCH$_3$, or SO$_3$.

The porphyrin must be present in a molar concentration greater than the sample manganese. Compounds I and IV, below, are preferred based on availability, solubility and sensitivity.

I = Diacetyladeuteroporphyrin IX dimethyl ester
IV = 5,10,15,20-tetrakis(4-trimethylammoninophenyl)porphyrin-tetra(toluene-4-sulfonate)

In general, the materials which can be used for color development are as follows:

DEVELOPER

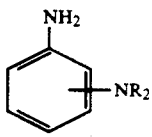

Positions 2 or 4

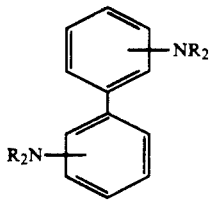

Positions 4,4′; 4,2′; 2,2′; or 5,5′

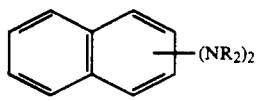

Positions 1,2; 1,4; 1,5; 1,7; 2,3; 2,6; or 2,8

Where R is H, CH$_3$, CH$_2$CH$_3$, CH$_2$CH$_2$OH, C$_6$H$_5$, CH$_2$CH$_2$CH$_3$ (or any combination).

In addition, the aromatic rings can be substituted with any number of X groups where X is H, Cl, Br, I, F, Cn, CH$_3$, CH$_2$CH$_3$, CH$_2$CH$_2$CH$_3$, OCH$_3$, OCH$_2$CH$_3$, C$_6$H$_5$ (or any combination).

COUPLER

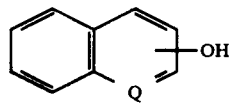

Where Q is CH, S, O or N and is not limited to any specific position within the ring.

In addition, the aromatic rings can be substituted with any number of X groups where X is H, Cl, Br, I, F, CN, CH$_3$, CH$_2$CH$_3$, CH$_2$CH$_2$CH$_3$, OCH$_3$, OCH$_2$CH$_3$, SO$_3$H, CO$_2$H, PO$_3$H, C$_6$H$_5$ (or any combination).

Optionally, a detergent can be added to enhance color development. Cationic detergents are preferred.

With respect to test strips or test devices, normally such strips or devices are formed by attaching a reagent pad to a substrate by means of glue or adhesive material. The reagent pads contain the active ingredients of the reagent for the determination which is to be made.

The substrate can be formed from any suitable material including polystyrene, polyvinylchloride, polyethylene, polycarbonate, etc. Preferably the substrate is flexible to facilitate manufacture. Typically, the test device will contain an elongated substrate such that one end of substrate can be used as a handle when the test device is dipped or contacted with the test fluid being analyzed. A preferred material is TRYCITE, polystyrene, made by Dow Chemical Company.

The glue or adhesive material employed to bind the reagent pads to the substrate can be any suitable material which is capable of bonding the pads to the substrate and readily adhering the different materials together. Double backed adhesive tape known as DOUBLE STICK, available from the 3M Company, is preferred.

Reagent pads can be formed from any suitable material. U.S. Pat. No. 3,846,247 teaches the use of felt, porous ceramic material and woven or matted glass fibers. Additionally, U.S. Pat. No. 3,552,928 teaches the use of woods, cloth, sponge material and argillaceous substances. The use of synthetic resin fleeces in glass fiber felts as a carrier matrix material is suggested in British Patent No. 1,369,139. Another British Patent No. 1,349,623, proposes the use of a light permeable meshwork of thin filaments as a cover for an underlying paper matrix. Polyimide fibers are taught in French Patent No. 2,170,397. Notwithstanding these suggestions, however, the material predominantly used in the art as a carrier matrix for the reagent pads and those which are especially useful in the present invention are bibulous paper, such as filter paper and porous hydrophilic film.

The reagent pad is normally impregnated with reagent material prior to bonding of the reagent pad to the substrate using the adhesive material.

EXAMPLE I

A. Dry reagent formulation
Part A
50 mL (milliliters) H$_2$O
7.0 g (grams) Dibasic Potassium Phosphate
Adjusts pH to 10.7
Part B
15 mg Diacetyladeuteroporphyrin IX dimethyl ester
25 mL DMF
Part C
0.88 g tetramethylbenzidine (TMB)
50 mL dimethylformamide (DMF)

Mix part A with C. Add 50 mL DMF followed by part B. Dip Whatman 3MM filter paper into the solution for 15 seconds. Remove and allow to air dry under controlled conditions of 20°–30° C. and 30–80% relative humidity.

B. A test solution was prepared by first making a manganese II diacetate aqueous solution. The solution was mixed part for part with a 5000 μg/L (micrograms per liter) aqueous solution of porphyrin IV and heated at 60° C. for 15 minutes. The 5000 μg/L solution was diluted with water to make a 2.0 μg/L test solution.

C. A dry reagent paper is dipped in the test solution. After five minutes, color change to blue is detected by eye.

EXAMPLE II

1.) TMB Indicator

Solutions:
0.01 M (molar) DBDH in ethanol
0.01 M Tetramethylbenzidine in ethanol 0.1 N NaOH $3\times10^{-5}$ M Manganese 5,10,15,20-tetrakis-(4-trimethylammon-10-phenyl)porphyrin-tetra(toluene-4sulfonate).

The reaction mixture included 1000 μL NaOH plus 200 μL DBDH plus 200 μL TMB plus 20 μL of (dilution of) manganese porphyrin solution.

An absorbance change was measured at 422 nm for initial two minutes of reaction. Absorbance is proportional to the manganese porphyrin concentration. A solution of 0.02 μg/L manganese gives an absorbance change of about 0.02.

2.) Dimethyl-p-phenylenediamine Indicator

Solutions:
0.01 M DBDH in ethanol
0.01 M N,N-dimethyl-p-phenylenediamine
0.01 M 8-hydroxy-quinoline
0.1 N NaOH
$3\times10^{-5}$ M manganese 5,10,15,20-tetrakis-(4-trymethylammon-10-phenyl)porphyrin-tetra(toluene-4sulfonate).

The reaction mixture included 1000 μL NaOH plus 200 μL DBDH plus 200 μL 8-hydroxyquinoline plus 200 μof N,N-dimethyl-p-phenylenediamine plus 20 μL of (dilution of) manganese porphyrin solution.

An absorbance change was measured at 620 nm for initial two minutes of reaction. Absorbance is proportional to the manganese porphyrin concentration.

EXAMPLE III

Coupled Indicator System

Indicators which have proved to be highly satisfactory with stable colors at high pH are the phenylenediamine developers with naphthol or hydroxyquinoline couplers. Among these compounds there are definite preferred combinations. To illustrate this a number of substituted 1-naphthols were evaluated with a number of p-phenylenediamines. They were evaluated as 500 micromolar solutions of the indicator in 0.1 M NaOH with 1% detergent (ethylquad 18/25 methylpolyoxyethylene(15)octadecyl ammonium chloride). The manganese 5,10,15,20-tetrakis( 2,6-dimethyl-3-sulfonatophenyl)porphine concentration was $10^{-8}$ M. The absorbance spectra were measured ten minutes after mixing the reagents.

The wavelength of maximum absorption is given in Table 1 and the difference in absorbance for the porphyrin containing sample from the blank is given in Table 2 for various combinations of developers and couplers.

TABLE 1

Wavelengths of maximum absorbance for combinations of phenylenediamines and naphthols

| developer | A | B | C | D | E | F | G | H | I | J | K | L | M | N |
|---|---|---|---|---|---|---|---|---|---|---|---|---|---|---|
| 1 | | | 562 | | 566 | | | 486 | 566 | | 562 | 522 | 516 | 582 |
| 2 | 626 | 632 | 608 | 656 | 624 | 632 | 650 | 580 | 622 | 638 | 588 | 536 | 552 | 624 |
| 3 | | | | | 568 | | | | 568 | | 512 | 522 | 516 | 580 |
| 4 | | | | | | | | | | | 574 | 518 | 528 | 604 |
| 5 | 622 | 632 | 596 | 656 | 612 | 632 | 624 | | 604 | 634 | 588 | 540 | 534 | 616 |
| 6 | | | | | | | | | | | | 518 | 514 | |
| 7 | | | 604 | | 644 | | | | 604 | | 596 | 514 | 512 | |
| 8 | 628 | 630 | 608 | 654 | 628 | 630 | 628 | 592 | 626 | 634 | 630 | 578 | 562 | 632 |
| 9 | 654 | 654 | 626 | 702 | 656 | 658 | | 614 | 620 | | 650 | 648 | 560 | 638 |

TABLE 2

Absorbance change from blank for combinations of phenylenediamines and naphthols.

| developer | A | B | C | D | E | F | G | H | I | J | K | L | M | N |
|---|---|---|---|---|---|---|---|---|---|---|---|---|---|---|
| 1 | | | 0.12 | | 0.32 | | | 0.22 | 0.28 | | 0.22 | 0.15 | 0.39 | 0.24 |
| 2 | 0.47 | 1.44 | 0.67 | 0.29 | 0.92 | 1.30 | 0.20 | 0.45 | 0.42 | 2.32 | 0.31 | 0.25 | 0.37 | 0.26 |
| 3 | | | | | 0.33 | | | | 0.29 | | 0.23 | 0.16 | 0.34 | 0.07 |
| 4 | | | | | | | | | | | 0.08 | 0.16 | 0.51 | 0.35 |
| 5 | 0.38 | 0.61 | 0.54 | 0.26 | 0.77 | 0.47 | 0.15 | | 0.37 | 1.58 | 0.18 | 0.29 | 0.46 | 0.21 |
| 6 | | | | | | | | | | | | 0.17 | 0.18 | |
| 7 | | | 0.30 | | 0.24 | | | | 0.32 | | 0.42 | 0.18 | 0.25 | |
| 8 | 0.48 | 1.04 | 0.72 | 0.25 | 1.07 | 0.89 | 0.29 | 0.89 | 0.59 | 1.52 | 0.79 | 0.28 | 0.54 | 0.53 |

TABLE 2-continued

Absorbance change from blank for combinations of phenylenediamines and naphthols.

| developer | A | B | C | D | E | F | G | H | I | J | K | L | M | N |
|---|---|---|---|---|---|---|---|---|---|---|---|---|---|---|
| 9 | 0.78 | 0.48 | 1.70 | 0.11 | 2.51 | 0.25 | | 0.79 | 1.21 | | 0.66 | 0.23 | 0.44 | 0.98 |

Key To Tables 1 and 2
Developers:
1 = 1,4-phenylene diamine
2 = N,N-diethyl-1,4-phenylenediamine sulfate
3 = 2-chloro-1,4-phenylenediamine
4 = 2-methoxy-1,4-phenylenediamine
5 = N,N-dimethyl-1,4-phenylenediamine
6 = 2,3,5,6-tetramethyl-1,4-phenylenediamine
7 = N-phenyl-1,4-phenylenediamine
8 = N,N-bis(2-hydroxyethyl)-1,4-phenylenediamine
9 = 4-N,N-diethyl-2-methylphenylenediamine
Developers showing no significant reactivity were:
2-nitro-1,4-phenylenediamine
N-4-methoxypenyl-1,4-phenylenediamine
Couplers:
A = 1-naphthol
B = 1-hydroxy-2-naphtholic acid
C = 2-methyl-1-naphthol
D = 1-naphthol-3,6-disulfonic acid
E = 4-methoxy-1-naphthol
F = 4-amino-1-naphthol
G = 4,5-dihydroxynaphthalene
H = 4-amino-5-hydroxy-1-naphthalene sulfonic acid
I = 5-amino-1-naphthol
J = 4-chloro-1-naphthol
K = 1,5-dihydroxy naphthalene
L = 6-amino-4-hydroxy-2-naphthalene sulfonic acid
M = 1,6-dihydroxynaphthalene
N = 1,7-dihydroxynaphthalene
Couplers showing no significant reactivity were:
2-nitroso-1-naphthol
2-nitro-1-naphthol
1,3-dihydroxy naphthalene It is clear from the data in Tables 1 and 2 that both the wavelength of maximum absorption and the magnitude of the absorbance are dependent on the phenylenediamine and the naphthol. Some combinations have much greater sensitivity than others.

In addition to the 1,4-phenylenediamines, 1,2-phenylenediamines were observed to give good colors. In addition to the 1-naphthols, 2-naphthols and hydroxy quinolines were observed to give good colors.

EXAMPLE IV

Various Porphyrins

Aqueous solutions of deuteroporphyrin IX 2,4-disulfonic acid dimethyl ester (A), meso-tetra(4-sulfonatophenyl)-porphine (B), tetra(N-methyl-4-pyridyl)porphine tetra tosylate (C), 5,10,15,20tetrakis(2,6-dimethyl-3-sulfonatophenyl)porphine (D) and uroporphyrin I dihydrochloride (E) were prepared. Ninety micromolar solutions of the porphyrin and manganese acetate were incubated at room temperature and at 80° C. for 24 hours. The absorbance spectra are shown in FIGS. 1-5. The solid lines are the room temperature samples and are identical to the initial mixture, the broken line the sample incubated at 80° C. The spectral changes produced by the intercalation of the manganese ion are quite apparent.

Tests of catalytic activity are given below. They were evaluated in 500 micromolar solutions of N,N-bis[2-hydroxyethyl]-1,4-phenylenediamine and 2-methyl-1-naphthol in 0.1 M NaOH with 1% detergent (ethylquad 18/25 methylpolyoxyethylene(15)octadecyl ammonium chloride). The manganese porphyrin concentration was $10^{-8}$ M. The reaction rates are from the absorbance change occurring in 45 seconds measured at 606 nm (nanometers).

TABLE 3

Reaction rates of various Porphyrins.
Porphyrin reaction rate (absorbance per second)

| blank | .0059 |
|---|---|
| A | .0080 |
| B | .0058 |
| C | .1472 |
| D | .1585 |
| E | .0092 |

It is surprising that porphyrin B gave no apparent activity, porphyrin A and E have a low reactivity while porphyrins C and D have very high activity. With higher concentrations of porphyrin B, its reactivity might be measurable.

EXAMPLE V

Lysed versus Unlysed Blood

A comparison of reactivity with unlysed blood showed that the reaction is catalyzed by the blood cells but with about 20% of the activity observed with a lysed sample.

The samples were evaluated as 500 micromolar solutions of N,N-bis(2-hydroxyethyl)-1,4-phenylenediamine and 2-methyl-1-naphthol in 0.1 M NaOH with 1% detergent (ethylquad 18/25 methylpolyoxyethylene(15)-octadecyl ammonium chloride). A 5 microliter sample of blood was used.

EXAMPLE VI

Effect of Oxidant and pH

It has been found that hydrogen peroxide is not a necessary reagent nor is a hydroperoxide but oxygen from air is a sufficient oxidant. This is demonstrated by the results from the following experiment.

CHEMVELOPE pH buffer, sodium carbonate and sodium bicarbonate sodium bicarbonate and tribasicphosphate and sodium dibasicphosphate and sodium tribasicphosphate, respectively, American Scientific Products) were used to provide pH 10, 11 and 12; 0 1 M NaOH was used to give approximately pH 13; and 1 M NaOH was used to give approximately pH 14. The reaction mixture was prepared by mixing 100, microliters of 10 millimolar oxidant in alcohol denatured with 5% methanol or 100 microliters of 3A alcohol for the air saturated experiment with 100 microliters of 5 millimolar aqueous N,N-bis(2-hydroxyethyl)-1,4-phenylenediamine and 5 millimolar alcoholic 2-methyl-1-naphthol with 700 microliters of base or buffer containing 1% detergent (ethylquad 18/25 methylpolyoxyethylene(15)octadecyl ammonium chloride). The manganese 5,10,15,20-tetrakis[2,6-dimethyl-3-sulfonatophenyl)porphine concentration was $10^{-8}$ M.

For the blank reaction the data is the absorbance change five minutes after the reagents were mixed. For the sample with manganese porphyrin, the data is the difference in absorbance change observed for the samples with the manganese porphyrin (from the blank).

TABLE 4

Dependence of Reactivity of Manganese Porphyrin on pH and Oxidant.

| pH or molarity of NaOH | air | | hydrogen peroxide | | DBDH | |
|---|---|---|---|---|---|---|
| | blank | Mn | blank | Mn | blank | Mn |
| 1.0M | 0.1743 | 0.0932 | 0.1381 | 0.0897 | 0.1664 | 0.1907 |
| 0.1M | 0.1666 | 0.0994 | 0.0967 | 0.0800 | 0.2048 | 0.1189 |
| 12 | 0.2088 | 0.0971 | 0.1150 | 0.1251 | 0.2731 | 0.0202 |
| 11 | 0.2509 | 0.0120 | 0.1481 | 0.0970 | 0.2616 | 0.0151 |
| 10 | 0.2449 | 0.0015 | 0.1560 | 0.0377 | 0.2665 | 0.0047 |

It is apparent from this data that the greatest sensitivity for manganese porphyrin is observed with the 0.1 M NaOH. The blank reaction increases as the pH decreases. Hydrogen peroxide lowers the blank reactivity. The oxidant is present at 1 millimolar in the reagent mixture while oxygen is present at about 0.25 millimolar. One would expect a dramatic increase in reactivity when the oxidant was added. This was not observed.

EXAMPLE VII

Effect of Oxygen

Since oxygen is the source of oxidation for this reaction, a dependence on oxygen concentration would be expected.

Air and oxygen saturated solutions were evaluated in 500 micromolar solutions of N,N-bis(2-hydroxyethyl)-1,4-phenylenediamine and 2-methyl-1-naphthol in 0.1 M NaOH with 1% detergent [ethylquad 18/25 methylpolyoxyethylene( 15)octadecyl ammonium chloride). The manganese 5,10,15,20-tetrakis(2,6-dimethyl-3-sulfonatophenyl)porphine concentration was $10^{-8}$ M. The blank reaction rate doubled when the solutions were oxygen saturated but the rate of the manganese porphyrin reaction was essentially unchanged. Thus, under these experimental conditions, oxygen does not limit the reaction rate.

EXAMPLE VIII

Assays of aqueous, urine and serum samples

Water and urine had manganese acetate added to give various manganese levels. The samples were mixed with an equal volume of tetra(N-methyl-4-pyridyl)porphine tetra tosylate and incubated for four hours at 80° C. An aliquot was then assayed with 500 micromolar solutions of N,N-bis(2-hydroxyethyl)1,4-phenylenediamine and 2-methyl-1-naphthol in 0.1 M NaOH with 1% detergent (ethylquad 18/25 methylpolyoxyethylene( 15)octadecyl ammonium chloride). If the absorbance change exceeded 0.5, the sample was diluted until the absorbance change was less than half an absorbance unit. The absorbances reported are the absorbance change in 45 seconds minus the absorbance of a blank. For manganese concentrations greater than 100 micrograms per liter, smaller sample volumes were used and the absorbance changes were scaled to correspond to the changes expected for a sample volume of 100 microliters.

TABLE 5

Reactions with urine and water samples.
Manganese Concentration in Micrograms/Liter

| | water | urine |
|---|---|---|
| 3 | 0.0381 | 0.0018 |
| 10 | 0.07715 | 0.0187 |
| 30 | 0.2041 | 0.06875 |
| 100 | 0.918 | 0.336 |
| 550 | 4.13 | 1.122 |
| 5500 | 14.7 | 16.5 |

The data shows an approximately linear dependence of the absorbance change on the concentration of manganese.

From the standard deviation calculated from replicated data, the standard deviation in manganese concentrations are 1.7 ug/L (microgram per liter) for water and 3.5 ug/L for urine samples with less than 10 ug/L total manganese concentration. This provides an estimate of the detection limit for a single determination.

A 300 microliter aliquot of serum was mixed with 700 microliters of a 100 micromolar solution of 5,10,15,20-tetrakis(2,6-dimethyl-3-sulfonatophenyl)-porphine and manganese acetate was added to give a concentration of 0.2 micromolar. This mixture was incubated at 80° C for twenty four hours. An 100 microliter aliquot was then assayed with 500 micromolar solutions of N,N-bis(2-hydroxyethyl)-1,4-phenylenediamine and 2-methyl-1-naphthol in 0.1 M NaOH with 1% detergent (ethylquad 18/25 methylpolyoxyethylene(15)octadecyl ammonium chloride). The absorbance at 615 nanometers after a two minute incubation was 0.2423 while a blank gave an absorbance of 0.0813. By calibration with manganese 5,10,15,20-tetrakis(2,6-dimethyl-3-sulfonatophenyl)porphine the concentration was calculated to correspond to 0.09 micromolar. The experiment shows that manganese in serum can be measured by this assay system. From the standard deviations in replication for the same experiment, the sensitivity of the assay to serum manganese porphyrin is 1.2 ug/L.

EXAMPLE IX

Assay of Blood for Manganese

Blood Samples were sent out for assay by flameless atomic absorption by Galbraith Laboratories, Inc., Knoxville, Tenn. 37921. An initial experiment showed that serum manganese levels were below the detection limit of the laboratory but that manganese in the red cell clot could be assayed. Thus, this experiment differs from the report of Strause and Saltman who assayed serum for manganese.

Twenty control samples from women without osteoporosis and eighteen samples from women with osteoporosis were obtained from the Cleveland Clinic. Data on the patients and samples is given in Tables 6 and 7.

Figure 6:
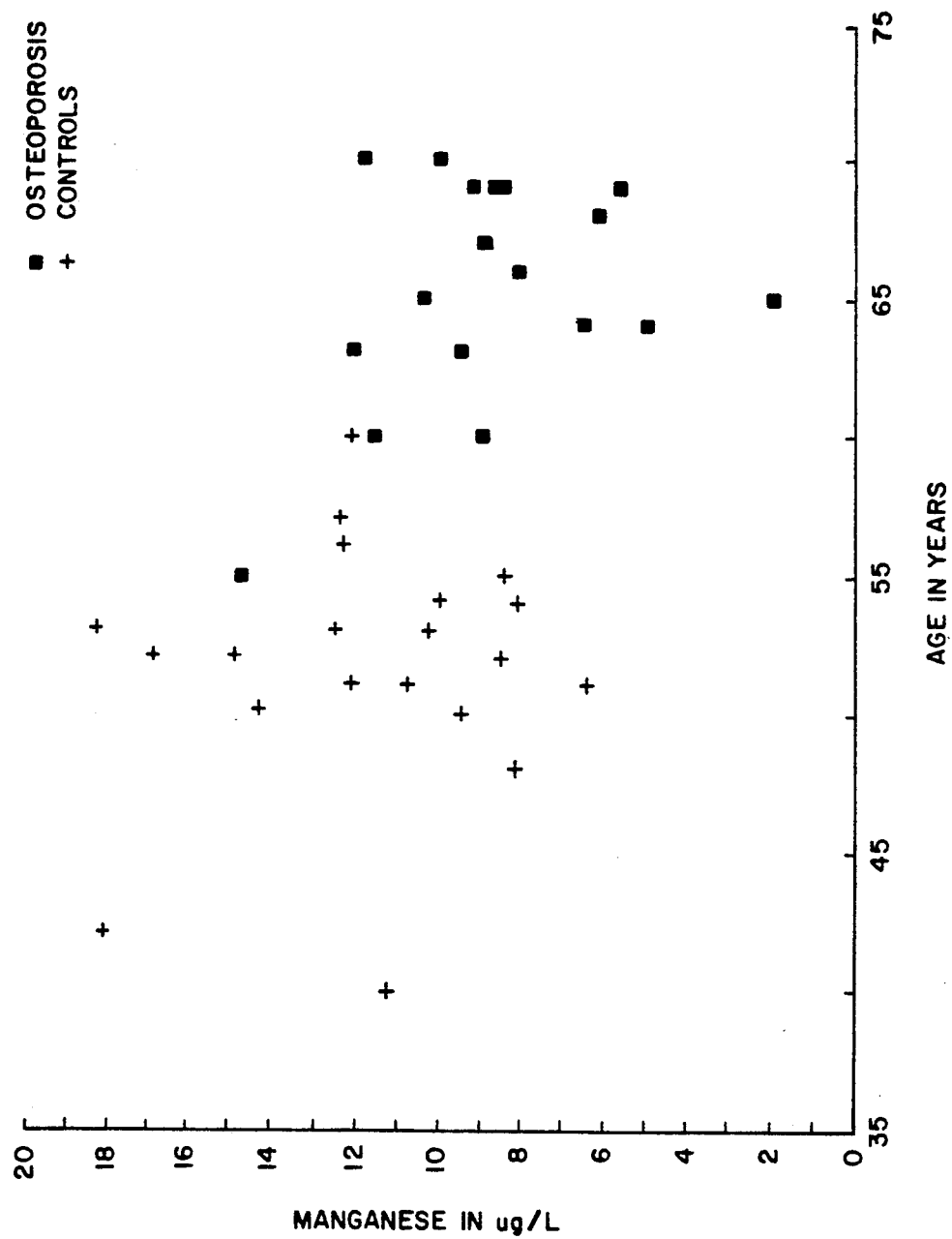
FIG. 6 is a plot of manganese concentrations and patient ages in accordance with the data in Example IX.

The manganese in the control samples was 11.77 (std. dev. 3.37) ug/L. The mean of the osteoporotic samples was 25% lower at 8.77 (std. dev. 2.99) and is statistically significantly different. The result supports the contention that manganese is lower in osteoporosis. Unfortunately, the two sample populations also are statistically different in age since age matched control samples for this study could not be obtained. The manganese concentrations and patient ages are plotted in FIG. 6. However, there is no statistically significant dependence of manganese concentration on patient age within either the controls or patients with osteoporosis. Some overlap of the manganese levels of the two populations is evident in the graph.

TABLE 6

| Data for Women with Osteoporosis. | | | |
|---|---|---|---|
| height (cm) | weight (kg) | age (years) | Mn (ug/L) |
| 152.3 | 80 | 67 | 9.0 |
| 150.0 | 57 | 70 | 10.0 |
| 160.8 | 65 | 68 | 6.1 |
| 149.3 | 49 | 69 | 8.5 |
| 160.3 | 62 | 64 | 6.5 |
| 152.2 | 66 | 63 | 9.6, 9.4 |
| 161.9 | 63 | 65 | <2 |
| 152.0 | 43 | 64 | 5.0 |
| 163.3 | 74 | 60 | 11.6 |
| 156.5 | 53 | 63 | 13.5, 10.7 |
| 156.2 | 73 | 55 | 14.7 |
| 152.3 | 53.5 | 69 | 9.2 |
| 154 | 62 | 69 | 8.7 |
| 153 | 69 | 69 | 5.6 |
| 147.1 | 52 | 70 | 11.9 |
| 168 | 67.5 | 66 | 7.5, 8.7 |
| 161.9 | 76.5 | 60 | 9.0 |
| 154.2 | 52 | 65 | 10.4 |

TABLE 7

| Data for Women without Osteoporosis. | | | |
|---|---|---|---|
| height (cm) | weight (kg) | age (years) | Mn (ug/L) |
| 164.4 | 68.8 | 52 | 8.5 |
| 154.5 | 59 | 51 | 12.1 |
| 167.6 | 86.2 | 51 | 6.4 |
| 163 | 62 | 42 | 18.1 |
| 170.2 | 66.7 | 52 | 16.9 |
| 172.7 | 72.6 | 52 | 14.9 |
| 147.3 | 54.4 | 50 | 9.5 |
| 168.9 | 57.6 | 54 | 8.1 |
| 160.0 | 75 | 60 | 12.1 |
| 159.6 | 63 | 56 | 12.3 |
| 167.6 | 63.5 | 40 | 11.3 |
| 162.5 | 61.3 | 53 | 10.3 |
| 166.4 | 80.3 | 54 | 10.0 |
| 165.1 | 71.2 | 48 | 8.2 |
| 161.3 | 52.2 | 51 | 10.8 |
| 162.6 | 64.9 | 50 | 14.3 |
| 172.1 | 95.3 | 53 | 18.3 |
| 170.3 | 72.5 | 57 | 12.4 |
| 166.3 | 54.4 | 55 | 8.4 |
| 166.2 | 55 | 53 | 12.5 |

From the foregoing, it will be seen that this invention is well adapted to all of the ends and objections hereinbefore set forth, together with other advantages which are obvious and inherent.

Obviously, many modifications and variations of the invention as hereinbefore set forth can be made without departing from the spirit and scope thereof and therefore only such limitation as should be imposed as are indicated by the appended claims.

What is claimed is:

1. A method for determining the manganese level in a blood test sample, said method comprising the steps of: lysing blood cells to obtain a blood test sample,
determining the manganese level of the test sample by combining the blood test sample with an assay composition comprising:
a porphyrin having a formula selected from the group consisting of

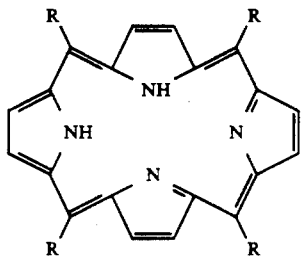

where R is

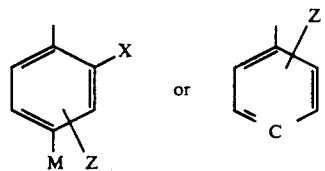

$X = CH_2$, $CH_2CH_3$, or $CH_2CH_2CH_3$;
$M = CO_2H$, $PO_3H_2$, or $SO_3H$;
$Z = H$, $CH_2$, $CH_2CH_2$, $CH_2CH_2CH_3$, $OCH_3$, $NO_2$, $CO_2H$, $NH_2$, Cl, Br, or F; and

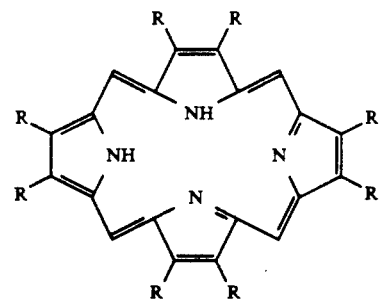

where each R is independently selected from $CH_2$, $CH_2CH_2CH_2CH_2CH_3$; $CH_2CH_2CO_2H$, $CH_2CH_2PO_2H_2$, $CH_2CO_2H$, $CH_2CH_2SO_3H$, $CH_2CH_2OH$, $CH_2CH_2NH_2$, $CH_2CH=CH_2$, $CHOHCH_3$, or $SO_3$;
a redox indicator; and
a buffer to maintain a pH of 11 to 14; and
determining any change in absorbance.

* * * * *

UNITED STATES PATENT AND TRADEMARK OFFICE
CERTIFICATE OF CORRECTION

PATENT NO. : 5,106,753
DATED : April 21, 1992
INVENTOR(S) : Marvin A. Genshaw and Michael J. Pugia It is certified that error appears in the above-identified patent and that said Letters Patent is hereby corrected as shown below:

Column 16, line 39, change "$CH_2$" to --$CH_3$-- (first occurrence)

Column 16, line 41, change "$CH_2$" to --$CH_3$-- and "$CH_2CH_2$" to --$CH_2CH_3$--

Column 16, line 56, change "$CH_2$" to --$CH_3$, $CH_2CH_3$--

Column 16, line 57, change "$CH_2CH_2CH_2CH_2CH_3$" to --$CH_2CH_2CH_3$--

Signed and Sealed this

Thirtieth Day of July, 1996

Attest:

BRUCE LEHMAN

Attesting Officer

Commissioner of Patents and Trademarks